US010314311B2

(12) United States Patent
Quidant et al.

(10) Patent No.: US 10,314,311 B2
(45) Date of Patent: Jun. 11, 2019

(54) MODIFIED SURFACE CAPABLE OF HAVING BACTERIOSTATIC AND BACTERICIDE ACTIVITY, THE METHOD FOR OBTAINING IT AND USE THEREOF

(71) Applicants: B. BRAUN SURGICAL, S. A., Rubi (ES); FUNDACIO INSTITUT DE CIENCIES FOTONIQUES, Castelldefels (ES); INSTITUCIO CATALANA DE RECERCA I ESTUDIS AVANCATS, Barcelona (ES)

(72) Inventors: Romain Quidant, Castelldefels (ES); Susana Santos, Castelldefels (ES); Pau Turon Dols, Rubi (ES); Sebastian Thompson, Castelldefels (ES); Christine Weis, Rubi (ES); Irene Prieto Martinez, Rubi (ES)

(73) Assignees: B. Braun Surgical, S.A., Rubi (ES); Fundacio Institut de Ciencies Fotoniques, Castelldefels (ES); Institucio Catalana de Recerca I Estudis Avancats, Barcelona (ES)

( * ) Notice: Subject to any disclaimer, the term of this patent is extended or adjusted under 35 U.S.C. 154(b) by 181 days.

(21) Appl. No.: 15/026,485

(22) PCT Filed: Oct. 1, 2014

(86) PCT No.: PCT/EP2014/071008
§ 371 (c)(1),
(2) Date: Mar. 31, 2016

(87) PCT Pub. No.: WO2015/049267
PCT Pub. Date: Apr. 9, 2015

(65) Prior Publication Data
US 2016/0227786 A1 Aug. 11, 2016

(30) Foreign Application Priority Data
Oct. 1, 2013 (EP) ..................... 13382384

(51) Int. Cl.
*A01N 59/16* (2006.01)
*A61L 31/16* (2006.01)
*A01N 25/34* (2006.01)

(52) U.S. Cl.
CPC ............. *A01N 59/16* (2013.01); *A01N 25/34* (2013.01); *A61L 31/16* (2013.01); *A61L 2300/404* (2013.01); *A61L 2300/606* (2013.01)

(58) Field of Classification Search
None
See application file for complete search history.

(56) References Cited

U.S. PATENT DOCUMENTS

| 4,442,133 A | 4/1984 | Greco et al. |
| 4,879,135 A | 11/1989 | Greco et al. |
| 2012/0059307 A1* | 3/2012 | Harris ............ A61K 8/0245 604/20 |
| 2013/0018299 A1 | 1/2013 | Ludwig et al. |
| 2013/0071619 A1* | 3/2013 | Kajikawa ............ B82Y 15/00 428/148 |

FOREIGN PATENT DOCUMENTS

| EP | 2241394 A1 | 10/2010 |
| WO | 2002089750 A2 | 11/2002 |
| WO | 2009024636 A1 | 2/2009 |
| WO | 2009044146 A1 | 4/2009 |
| WO | 2010107720 A2 | 9/2010 |
| WO | 2012027728 A2 | 3/2012 |
| WO | 2012031282 A2 | 3/2012 |
| WO | 2012059944 A2 | 5/2012 |

OTHER PUBLICATIONS

Ferrari et al., J Colloid and Interface Science; 347 (2010); pp. 15-24; published Mar. 7, 2010.*
Morones, J. et al., "Room temperature synthesis of an optically and thermally responsive hybrid PNIPAM-gold nanoparticle," Journal of Nanoparticle Research, 2010, 12, 1401-1414.
Maity, S. et al., "Embedded metal nanoparticles as localized heat sources: An alternative processing approach for complex polymeric materials," Polymer, 2011, 52, 1674-1685.
Zeng, N. et al., "Heat generation by optically and thermally interacting aggregates of gold nanoparticles under illumination," Nanotechnology, 2009, 20, 8 pages.
Concise Description of Relevance filed Oct. 25, 2016, with the Third-Party submission for U.S. Appl. No. 15/026,485.
Kisko et al., "Biofilm removal of Pseudomonas strains using sanitation," Acta Univ. Sapientiae, Alimentaria, 2011, 4, 69-79.
Scher et al., "Effect of Heat, Acidification, and Chlorination on *Salmonella enterica* Serovar Typhimurium Cells in a Biofilm Formed at the Air-Liquid Interface," Applied and Environmental Microbiology, 2005, 71, 1163-1168.
Arguelles, "Thermotolerance and trehalose accumulation induced by heat shock in yeast cells of Candida albicans," FEMS Microbiology Letters, 1997,146, 65-71.
Written Opinion of International Searching Authority with International Search Report from PCT/EP2014/071008, dated Nov. 24, 2014, 8 pages.

(Continued)

*Primary Examiner* — Jeffrey T. Palenik
(74) *Attorney, Agent, or Firm* — Barnes & Thornburg LLP

(57) ABSTRACT

The present invention relates to a modified surface capable of having bacteriostatic and bactericidal activity when it is light irradiated, thus converting the surface of the substrate into a bacteriostatic and a bactericidal surface as many times as it is desired, and for a long time. According to the invention, the modified surface upon light irradiation avoids the attachment of a microorganism to this surface, inhibits the formation of a biofilm on this surface and destroys an already formed biofilm on this surface. These effects can be achieved as many times as it is desired, and for indefinite time.

18 Claims, 4 Drawing Sheets

(56) References Cited

OTHER PUBLICATIONS

Morones, J. Ruben, and Wolfgang Frey. "Room temperature synthesis of an optically and thermally responsive hybrid PNIPAM-gold nanoparticle." Journal of Nanoparticle Research 12.4 (2010): 1401-1414.†

Maity, Somsubhra, et al. "Embedded metal nanoparticles as localized heat sources: An alternative processing approach for complex polymeric materials." Polymer 52.7 (2011): 1674-1685.†

Zeng, Nan, and Anthony B. Murphy. "Heat generation by optically and thermally interacting aggregates of gold nanoparticles under illumination." Nanotechnology 20.37 (2009): 375702.†

\* cited by examiner
† cited by third party a)

b)

FIG 9  FIG 10
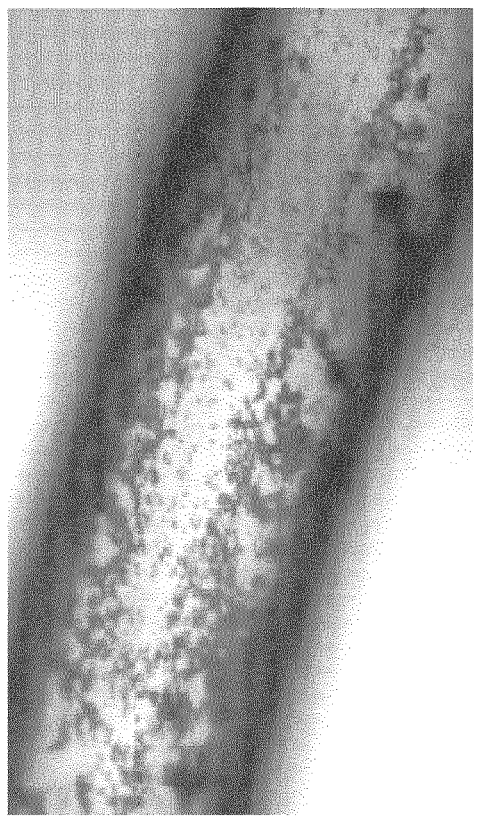 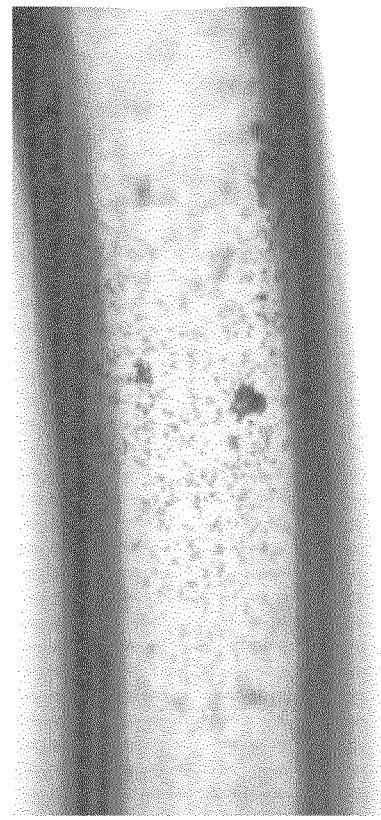

MODIFIED SURFACE CAPABLE OF HAVING BACTERIOSTATIC AND BACTERICIDE ACTIVITY, THE METHOD FOR OBTAINING IT AND USE THEREOF

CROSS-REFERENCE TO RELATED APPLICATIONS

This application is the U.S. national phase of PCT/EP2014/071008, filed on Oct. 1, 2014, which claims priority to European Patent Application No. 13382384.9, filed on Oct. 1, 2013. The disclosures of both European Patent Application No. 13382384.9 and PCT Application No. PCT/EP2014/071008 are hereby incorporated herein by reference in their entireties.

FIELD OF THE INVENTION

The present invention relates to a modified surface capable of having bacteriostatic and bactericidal activity. In particular, the present invention relates to a novel modified surface which upon light irradiation converts the surface of a substrate having said modified surface into a bacteriostatic and a bactericidal surface. The present invention also relates to a method for modifying the surface of a substrate in order to be able to have a bacteriostatic and bactericidal activity when it light irradiated and also relates to a medical or non-medical device having said modified surface. The modified surface according to the present invention is suitable for avoiding the attachment of a microorganism to this surface, inhibiting the formation of a biofilm on this surface and/or destroying an already formed biofilm on this surface when it is light irradiated. These effects can be achieved as many times as it is desired, and for indefinite time, without delivering neither an antimicrobial agent nor a pharmaceutical agent such as an antibiotic or a drug, respectively.

BACKGROUND OF THE INVENTION

Organisms that adhere to, for example, the catheter surface maintain themselves by producing an "extracellular slime," a substance rich in exopolysaccharides, often referred to as fibrous glycocalyx or microbial biofilm. Microorganisms bind to the surface of host proteins, such as fibrin and fibronectin, to produce biofilm. The organisms embed themselves in the biofilm layer become more resistant to antimicrobial agents and therapies. The use of lumen flush solutions including a combination of antimicrobial agents as well as anti-coagulants is a known process for removing them.

Another strategy has been to impregnate the surfaces of said catheters with antimicrobial agents in order to prevent colonization and the formation of biofilm. An improved approach for prevention of intravascular catheter-related infections is desired.

A considerable amount of attention and study has been directed toward preventing colonization of bacterial and fungal organisms on the surfaces of orthopedic implants by the use of antimicrobial agents, such as antibiotics, bound to the surface of such devices. The objective of such attempts has been to produce a sufficient bacteriostatic or bactericidal action to prevent colonization. Various methods have previously been employed to coat the surfaces of medical devices with an antibiotic.

U.S. Pat. No. 4,442,133, invented by Greco et al., discloses a method to coat the surface of medical devices with antibiotics involving first coating the selected surfaces with benzalkonium chloride followed by ionic bonding of the antibiotic composition.

U.S. Pat. No. 4,879,135, invented by Greco et al., discloses surface modification of surgical implants by binding of drugs which, after implantation, are slowly released. More particularly, it relates to improved surgical implants having sustained, localized delivery of pharmacological agents such as extended antibiotic activity or reduced thrombogenicity, and methods for producing same. The surface modification of surgical implants by the adhesion thereto of pharmacological agents for the purpose of minimizing infection and prosthesis rejection is well-known and has generated broad interest for some time.

A biofilm is an accumulation of microorganisms including bacteria, fungi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing.

Biofilms are remarkably resistant to treatment with conventional topical and intravenous antimicrobial agents. This is thought to be due to the antibiotic's inability to penetrate the polysaccharide coating of the biofilm.

Bacteria and other microorganisms embedded within biofilms are also resistant to both immunological and non-specific defense mechanisms of the body. Bacterial contact with a solid surface triggers the expression of a panel of bacterial enzymes that cause the formation of polysaccharides that promote colonization and protection of the bacteria.

The polysaccharide structure of biofilms is such that immune responses may be directed only at those antigens found on the outer surface of the biofilm and antibodies and other serum or salivary proteins often fail to penetrate into the biofilm.

Also, phagocytes may be effectively prevented from engulfing a bacterium growing within a complex polysaccharide matrix attached to a solid surface.

Many different medical devices may lead to infection when in contact with a body tissue or fluid. Exemplary of such devices are vascular access (arterial and venous) catheters, introducers, vascular grafts, urinary catheters and associated devices, such as drainage bags and connectors, and abdominal cavity drainage tubing, bags and connectors, and many others.

WO200289750 relates to a photodynamic therapy utilizing a pyrrolnitrin. In particularly, it relates to improved surgical implants having sustained, localized delivery of pharmacological agents such as extended antibiotic activity or reduced thrombogenicity, and methods for producing same. More particular, it discloses a method of photoeradication of cells and acellular organisms, such as during an in vitro or in vivo disinfection or sterilization procedure, or for cancer cell or acellular organism eradication. In one embodiment, the method utilizes a combination of a photosensitive material, pyrrolnitrin, and a chemical agent, such as a surfactant material, in a solution. In accordance with this international patent application, a photodynamic therapy utilizing a photosensitive material, such as methylene blue, methylene green, or toluidene blue, in combination with pyrrolnitrin, and a light emitting device, such as a light wand, light patch, light pad or shaped light-emitting or light-communicating article is described.

The nanoparticles are used widely at present, especially in the field of nanotechnology for biomedical treatment. These nanoparticles need to reach the pathological region and go through extremely small holes inside the body. For example, if it is necessary to transport the gold nanoparticles to malignant tumors through holes of approximately 100 nm formed at the connection branch points between the pre-existing blood vessels and the new blood vessels produced by those malignant tumors. The rod-shaped gold nanoparticles will encounter difficulties reaching the area of pathology due to their shape.

The European Patent No. EP2241394 discloses a gold nanoparticle composition that can pass through small holes in vivo more readily than a rod-shaped gold nanoparticle, and that can be utilized as a self-heating energy acceptor.

The International Patent Application No. WO2009/024636 relates to a photothermal treatment. More particularly, it discloses an encapsulated hybrid material. That encapsulation in silica is particularly advantageous in the measurement to control the textural parameters of the cover and at the same time offers many opportunities for functionalization. It is especially suitable for the incorporation of gold nanoparticles in a mesoporous silica matrix, which allow a high pore management with controllable pore size and high surface area. The hybrid material allows the anchor of a drug and/or biomarker on the surface of silica that forms the nanospheres. The hybrid material contains at least two components: gold nanoparticles, of size between 10 and 60 nm, within a matrix of an inorganic compound, preferably silicon. The light absorbed by the nanoparticles is rapidly converted into heat. The incorporation of two or more gold nanoparticles within a capsule involves the interaction between them against electromagnetic stimuli which allows their use as diagnostic tools, control of drug release or photothermal treatments.

The patent application US20130018299 discloses nano-constructs comprising nanoshells and methods of using the nano-constructs for treating or ameliorating a medical condition. More particularly, a method of forming degradable nanoshells on a polymeric core substrate is described. The nanoshells include a metal, carbon, or a conducting polymer. The nano-constructs can be administered to a target tissue of a subject, which can be human or an animal. An energy source can be applied to the nano-constructs. The nano-constructs absorb the energy and then translate the energy into heat, thereby providing therapy via delivering a drug contained into said nano-constructs to the subject. The light activates the drug delivery.

The International patent application WO2010/107720 describes a system for energy upconversion and/or down conversion and a system for producing a photostimulated reaction in a medium. The nanoparticle described is configured, upon exposure to a first wavelength $\lambda_1$ of radiation, to generate a second wavelength $\lambda_2$ of radiation having a higher energy than the first wavelength $\lambda_1$. The system is designed for producing a photostimulated reaction in a medium. Furthermore, that system includes a receptor disposed in the medium in proximity to the nanoparticle which, upon activation by the second wavelength $\lambda_2$, generates the photostimulated reaction. Therefore, again the emission light ($\Delta_2$) causes the activation of a determinate reaction. Thus, these particles are configured to convert the incident light into a different emitted light.

Therefore, it is still the need to provide a novel way of infection prevention, biofilm inhibiting and/or biofilm destroying which will be adequate for any type of substrate, which properties will be maintained for a long term, and specially without delivering an antimicrobial agent nor a pharmaceutical agent such as an antibiotic or a drug, respectively.

SUMMARY OF THE INVENTION

The present invention was made in view of the prior art described above.

The object of the present invention is to provide a modified surface capable of having bacteriostatic, bactericidal and antimicrobial activity in an easily, reliably and non-harmful way for human or animal applications, as well as to provide a method for modifying a surface to be able to have a bacteriostatic and bactericidal activity for a long term, every time that it is light irradiated. The invention also relates to a medical or non-medical device having said modified surface which when it is light irradiated avoids the attachment of a microorganism to this surface, inhibits the formation of a biofilm on this surface and/or destroys an already formed biofilm on this surface.

To solve the problem posed by the prior art, the present invention provides a modified surface which is capable to convert the surface of a substrate, which comprises said modified surface, into a bacteriostatic and bactericidal surface when it is light irradiated, thus, avoiding the attachment of a microorganism to this surface, inhibiting the formation of a biofilm on this surface and/or destroying an already formed biofilm on this surface. More particularly, it is claimed a modified surface capable of having bacteriostatic and bactericidal activity which comprises:

a substrate configured to anchor thermal nanoparticles supporting local surface plasmon resonance; and, thermal nanoparticles supporting local surface plasmon resonance bonded to said substrate forming a thermal coating, the thermal nanoparticles being able to increase their temperature by light irradiation in a wavelength range that matches with the wavelength of the local surface plasmon resonance of said nanoparticles, whereby said thermal coating rises its temperature, allowing the temperature rise of said thermal coating to avoid the attachment of a microorganism to this surface, to inhibit the formation of a biofilm on this surface and/or to destroy an already formed biofilm on this surface.

Surprisingly, said modified surface becomes a bacteriostatic and bactericidal surface when it is light irradiated within the wavelength range that matches with the wavelength of the local surface plasmon resonance of said nanoparticles, for a long time, every time it is light irradiated.

The term "surface plasmon resonance" (SPR) refers to the collective resonant oscillation of electrons of the material excited by incident light (light irradiation). The resonance condition is established when the frequency (wavelength range) of light matches or couples the natural frequency (wavelength band) of quasi-free electrons oscillating against the restoring force of positive nuclei. SPR in nanometer-sized nanoparticles (<100 nm diameter) is also called localized or local surface plasmon resonance (LSPR).

The term "light irradiation" or "light irradiated" means the range of optical wavelengths used to rise the temperature of the thermal nanoparticles. The wavelengths of this light should overlap with the wavelength plasmon resonance of the nanoparticle. For surgical implants the irradiated wavelength range is preferable within 750-1200 nm.

The term "thermal nanoparticle" means herein a plasmonic nanoparticle engineered to generates an electric field inside of the nanoparticle upon light irradiation. The thermal nanoparticle is a plasmonic nanoparticle engineered to absorb into the nanoparticle the incident light upon light irradiation and mainly dissipate into the ions network the light intercepted by the nanoparticles and the corresponding energy stored in the electron cloud, generating a heating on the nanoparticle.

Therefore, the thermal nanoparticle, which is a plasmonic nanoparticle, is configured to generate an electric field inside of the nanoparticle when it is light irradiated. Thus, the generated electric field (E) inside of the nanoparticle is responsible of the heat generation of the nanoparticle, and the power of heat generation (Q) inside the nanoparticle is directly proportional to the absorption cross-section ($\sigma_{ABS}$).

The material of said thermal nanoparticles may be any one provided that supports (local) surface plasmon resonance. Examples of these materials are a metal, a semiconductor, an oxide, a metal oxide or a combination thereof, preferable being gold, silver or copper.

Said thermal nanoparticles may has a particle size ranging from 1 nm to 1 µm, more preferable from 1 nm to 100 nm.

Said thermal nanoparticles has a shape selected from a cylindrical, triangular, pyramidal, cubic, spherical, star shape, rod shape or a combination thereof. Any other shape is also contemplated into the scope of the present invention provided that it allows generating the electric field (E) inside of the nanoparticle when it is light irradiated.

Advantageously, the behaviour of light in a thermal nanoparticle, which is bonded or decorated on a substrate according to the present invention, is of linear interaction, that is, the energy of the emitted light (after interaction) is equal to the energy of the incident light. In a linear interaction (LI), the dielectric polarization (P) responds linearly to the electric field (E) of the light.

Furthermore, the oscillation of electrons of said thermal nanoparticles stimulated by the light irradiation causes an increase of the nanoparticle temperature, whereby the thermal coating, which comprises said thermal nanoparticles, is additionally heated by thermal diffusion.

The rise in temperature of said coating, which comprises said thermal nanoparticles, induces the destruction or alteration of the extracellular polymeric substances which are used by microorganisms for adhering to the surface, thus preventing their attachment to the surface. Further, this rise in temperature of the modified surface also destroys the microorganisms already adhered to the surface thus producing inhibition of the creation of a biofilm.

Advantageously, with the modified surface according to the first aspect of the present invention, it is provided a novel way of infection prevention, biofilm inhibiting and biofilm destroying adequate for any substrate, which is configured to anchor said thermal nanoparticles supporting local surface plasmon resonance, as many times as it is desired, and for an indefinite term, without delivering an antimicrobial agent, nor a pharmaceutical agent.

The thermal plasmonic nanoparticles may be anchored on a substrate by different ways. For example, the thermal nanoparticles may be anchored via a covalent bond using a functional molecule, or via an electrostatic interaction, or via a complexing reaction. A combination of these different ways to anchor nanoparticles on a substrate is also contemplated in the scope of the present invention. The functional molecule is a bi-functional molecule or a functional molecule having at least two reactive endings.

Therefore, according to the first aspect of the present invention, it is provided a modified surface (thermal coating) that acts as a plasmonic meta-surface that supports surface plasmons to which light couple.

Surprisingly, the authors of the present invention have found that the temperature rise of the thermal coating is enough higher to cause the destruction of a biofilm already formed on the surface. In the three circumstances above, the light irradiation within a selected wavelength spectrum provides the temperature rise of the plasmonic nanoparticle's electrons, whereby rises the temperature of the thermal coating, enough to convert the modified surface into a bacteriostatic and bactericidal surface, which prevents the attachment of a microorganism to this surface, inhibits the formation of a biofilm on this surface and/or destroys an already formed biofilm on this surface.

When, the bacteriostatic and bactericidal activity is directed to surgical implants for human applications, the light irradiation is preferable in the infrared spectrum in order reduce damage in the surrounded healthy tissue. Only as reference, the correspondence of the wavelength with the photon energy is shown in the table included below.

| Light comparison | | | |
| --- | --- | --- | --- |
| Name | Wavelength | Frequency (Hz) | Photon Energy (eV) |
| X-Ray | 0.01 nm-10 nm | 30 EHz-30 PHz | 124 eV-124 keV |
| Ultraviolet | 10 nm-380 nm | 30 PHz-790 THz | 3.3 eV-124 eV |
| Visible | 380 nm-700 nm | 790 THz-430 THz | 1.7 eV-3.3 eV |
| Infrared | 700 nm-1 mm | 430 THz-300 GHz | 1.24 meV-1.7 eV |
| Microwave | 1 mm-1 meter | 300 GHz-300 MHz | 1.24 µeV-1.24 meV |

The present inventors have found that a modified surface of a substrate according to the first aspect provides a surface capable of having bacteriostatic and bactericidal activity upon light irradiation within a determinate wavelength range, in a different way from that of the conventionally used antimicrobial agents, antibiotics, which are attached to the surface of substrates, or in a different way from that of the conventionally used pharmacological agents which have a sustained and localized delivery of said agents, which deliver a photosensitive material, the photosensitive material being activated by a photothermal therapy.

The modified surface provided according to the first aspect of the present invention is easily, reliably and non-harmful for surgical implants or medical devices in general. The modified surface according to the first aspect is also applicable in a non-medical device, being the non-medical device, for example, kitchen surfaces, piping, toys, or any other substrate susceptible to be sterilized or cleaned in the sense of destroying an already formed biofilm on this surface or preventing a microorganism attached to the surface.

Therefore, a rise of temperature (ΔT positive) of the thermal coating caused by a light irradiation with a predetermined wavelength range allows converting the modified surface into a bactericidal and bacteriostatic surface. Advantageously, the bacteriostatic and bactericidal activity may be maintained for a long term. Moreover, the bacteriostatic and bactericidal activity of the substrate thus decorated may be remembered by light irradiating again within the predetermined wavelength spectra, until the activity is needed.

Advantageously, the rise of temperature of the modified surface may be controlled by the type of material, size and shape of the thermal nanoparticles, by the density of thermal nanoparticles anchored on the substrate, and by the intensity of the light applied, which is governed by the source to irradiate the light.

Furthermore, the rise of temperature of the modified surface may be as local as it is desired by delimiting the area to be irradiated.

There is not limitation in the type of material of the substrate. The only condition is that the material of the substrate be able to anchor a surface plasmon nanoparticle on the substrate, directly, or by previously preparing the substrate or the nanoparticle. Preferable, the substrate is of fiber, woven, an alloy, a steel, a plastic, a glass, a ceramic material, a polymer, a resin or a combination thereof.

The substrate may be also a textile fabric, along woven, knits, braids and non-woven fabrics.

The polymers useful for a medical device are such as along polypropylene, polyethylene, low-density polyethylene, high density polyethylene, high-molecular-weight polyethylene, ultra-high-molecular-weight polyethylene, polyethylene terephtalate, polypropilene terephtalate, polybutylen terephtalate, polytetrafluorethylene and the like. Furthermore suitable absorbable polymers can be used.

As stated above, the structural parameters of the nanoparticle (shape, dimension, material) determine the spectral features of the plasmon resonance (central wavelength, bandwidth of the resonance etc. . . . ). In that sense, the optical wavelength has to be adapted to the LSPR of the nanoparticle and vice versa. Although note that a reason for moving the plasmon resonance and thus the illumination to a specific region of the spectrum may be to avoid photodamage of the surface to be treated, especially in a body.

Any light source which is capable to generate the optical wavelength within the desirable wavelength spectrum (LSPR) of the thermal nanoparticle is susceptible to be used to irradiate the modified surface. Without the intention to limit the possible sources and only as mere exemplary, a fluorescent or halogen lamp, a laser, an intense pulsed light, a light-emitting diode, an incandescent or chemiluminescence's light or a combination thereof are described herein.

For medical applications, the light irradiated is preferable within the infrared spectrum because the human tissue is transparent to the infrared light down to a few centimeters deep. Therefore, it is possible to rise the temperature of the modified surface by light irradiation, for example, from outside of a body.

In a second aspect, the present invention relates to a method for modifying a surface capable of having bacteriostatic, bactericidal and antimicrobial activity according to the first aspect, the method comprising:
preparing a substrate for anchoring thermal nanoparticles supporting local surface plasmon resonance;
selecting thermal nanoparticles supporting local surface plasmon resonance; and
bonding the selected thermal nanoparticles to said substrate thereby forming a thermal coating,
the thermal nanoparticles being able to increase their temperature by light irradiation in a wavelength range that matches with the wavelength of the local surface plasmon resonance of said nanoparticles, whereby said thermal coating rises its temperature, allowing the temperature rise of said thermal coating to avoid the attachment of a microorganism to this surface, to inhibit the formation of a biofilm on this surface and/or to destroy an already formed biofilm on this surface.

The preparation of the substrate may include one or more of the following treatments when it is required activate or functionalize the substrate:
activating the surface of the substrate by a surface modification method;
functionalising the surface of the substrate with a functional molecule, which has at least two reactive endings; and
functionalising the surface of thermal nanoparticles with a functional molecule, which has at least two reactive endings.

It is understood by the description herein to the fact that there are substrates that do not require to be activated nor to be functionalized.

The surface modification methods for activating the surface are described herein, the cold plasma polymerization being preferable. The ways to functionalize the surface are described herein, a diamine derivative as functional molecule being preferable.

The ways to bind the thermal nanoparticles to said substrate are also described herein.

The material and the structural parameters of the thermal nanoparticle, as well as the wavelength range to be irradiated are also described herein.

In a third aspect, the present invention relates to a medical device or to a non-medical device comprising the modified surface according to the first aspect of the present invention, so that the medical device or the non-medical device comprises the thermal coating capable of having bacteriostatic and bactericidal activity upon light irradiation, thus avoiding the attachment of a microorganism to this surface, inhibiting the formation of a biofilm on this surface and/or destroying an already formed biofilm on this surface.

BRIEF DESCRIPTION OF THE DRAWINGS

For better understanding of what has been disclosed some drawings are attached in which, schematically and solely by way of non-limiting example, show a practical case of embodiment.

FIGS. 7 to 10 are intended to show the inhibition, destruction and the prevention of the microorganism attachment to the modified surface according to the present invention.

FIG. 7 shows a Biofilm formation in blue color (shadow surrounding threads of the mesh) on the modified mesh after bacteria incubation, and without any light irradiation.

FIG. 8 shows a biofilm inhibition and biofilm destruction on the modified mesh after light irradiation in wavelength range of 750-1200 nm, wherein the plasmon wavelength of the thermal plasmonic nanoparticle which is bound to the substrate is a wavelength of 840 nm.

FIG. 9 shows microorganisms attached to a thread of a modified surface mesh in blue color (marks).

FIG. 10 shows the prevention of the microorganism attachment to the modified surface mesh after been light irradiated in wavelength range of 750-1200 nm which couples with 840 nm wavelength, which is the plasmon wavelength of the thermal plasmonic nanoparticle which has bonded to the surface.

DETAILED DESCRIPTION OF THE INVENTION

Figure 1:
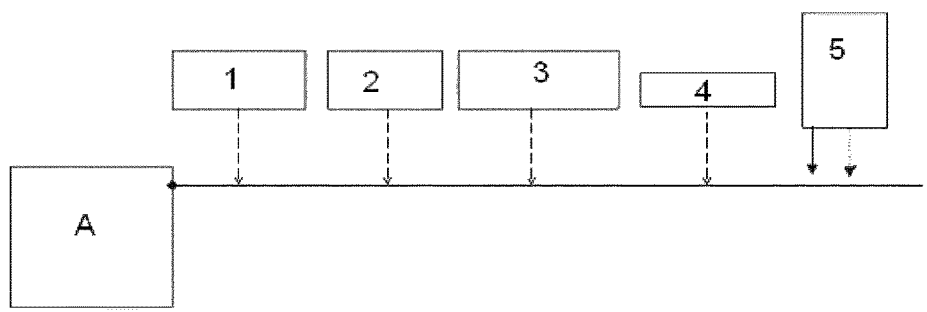
FIG. 1 is a block diagram schemating the steps of the method for modifying a surface of a substrate (A) according to a particular embodiment of the present invention. In this embodiment, the substrate (A) was prepared activating the surface by cold plasma polymerization (1), then, fictionalizing (2) the surface with diamine groups, and finally anchoring or bonding (3) thermal nanoparticles to form a thermal coating. The substrate having the modified surface was implanted (4), for example in a body, and then, light irradiated with Laser/IPL (5).

In order to configure a substrate to be able to anchor a thermal surface plasmon nanoparticle to which light can be coupled, the substrate may be previously activated using any surface modification method known in the art. Only as mere exemplary, physic-chemical methods such as a treatment with active gases and vapors or irradiation (plasma); deposition of polymers from active gases and vapors (chemical vapor deposition); active gas or accelerated ion treatments (Gas phase oxidation with ozone, ion beam); crosslinking of surface molecules; or mechanical methods such as roughening; or chemical methods such as physical absorption, chemical conjugation to surface groups, chemical modification of the surface; or graft polymerization with radiation initiation or chemical initiation; or coating of the surface with an active component or coating matrix which contains active component are described herein.

There are substrates that do not need to be activated because they are already activated by, for example, its natural condition. In order to identify when the substrate is or not activated the skill in the art known common measurements such as the contact angle measurement wherein the angle between the surface and a water droplet is measured. In view on this data the surface energy could be calculated. Another way is to let the surface react with a known chromophore and measure the attached quantity comparing to a calibration curve.

The substrate or the thermal surface plasmon nanoparticle may also contain functionalized groups or they are functionalized by an activation process, with reactive groups: —COOH (carboxylic acids), —CHO (aldehyde), —NH$_2$ (amine), —CONH$_2$ (amide), —CN (nitril), —OH (alcohol), —SH (thiol), etc. . . . . In general: fluoro, chloro, bromo, iodo, carbaldehyde, keto, carboxyl, cyano, nitro, amido, hydroxyl, amino, sulfato, sulfito, phosphato, phosphito, hydrolyl, oxy, mercapto or thio; or Complex forming groups; Groups able to form hydrogen bonds; Molecules containing ionic groups for ionic adsorption. Examples of alternatives are common crosslinkers like the imidoester crosslinker dimethyl suberimidate, the N-Hydroxysuccinimide-ester, formaldehyde, glutaraldehyde, etc. or the like.

Thus, the substrate or the thermal surface plasmon nanoparticle may be previously functionalised with a functional molecule, preferable a bi-functional molecule or a functional molecule having at least two reactive endings. The functional molecule is a crosslinker that must have at least two reactive endings, allowing at least the first reactive end group to be able to anchor the substrate previously or not activated and the at least the second reactive end group to be able to anchor the surface plasmon nanoparticle. Only as mere exemplary, the following reactive endings are described herein for anchoring the surface plasmon nanoparticle to the substrate: —COOH (carboxylic acids), —CHO (aldehyde), —CONH$_2$ (amide), —CN (nitril), —OH (alcohol), —SH (thiol) etc. In general: fluoro, chloro, bromo, iodo, carbaldehyde, keto, carboxyl, cyano, nitro, amido, hydroxyl, amino, sulfato, sulfito, phosphato, phosphito, hydroxyl, oxy, mercapto or thio; or Complex forming groups; Groups able to form hydrogen bonds; Molecules containing ionic groups for ionic adsorption. Examples of alternatives are common crosslinkers like the imidoester crosslinker dimethyl suberimidate, the N-Hydroxysuccinimide-ester, formaldehyde, glutaraldehyde, etc. Other commercially available bi-functional crosslinkers may be a boc-amino, ethanthiol, mercapto-1-butanol, etc.

Therefore, the surface of the plasmonic nanoparticles can be also modified in order to bond to the substrate as described herein. This modification can be performed by using hereto- or homo-functional molecules able to bind on one side to the nanoparticle's surface and on the other side to the substrate, e.g. the modification of a gold surface with thiol containing reagents which has on the other side the desired functional group able to bind to the substrate either covalently or by ionic interaction. These hereto- or homo-functional molecules include all the HS—R-functional groups, where —R relates to any alkyl or polyethylenglycol chain and the functional groups relates to any chemical group able to be activated and coupled to the substrate surface. Especially HS—R—COOH, HS—R—HN$_2$, HS—R—SH, HS—R—SO$_3$, and HS—R—N(CH$_2$)$_3^+$ are suitable for the purpose of the present invention. The thermal nanoparticle's surface can also be modified by polyvinylpirrolidone and a large number of polymers.

By the other hand, there are substrates which do not require to be activated, neither require the use of a functional molecule. These substrates can be a polymer or a co-polymer which have active groups, such as free amino groups, in their surface. These active groups can directly anchor a thermal surface plasmon nanoparticle without the need to previously prepare the substrate. Preferably the anchoring method is not reversible.

The anchorage of a thermal surface plasmon nanoparticle to the substrate may be carried out by a covalent bond via a functional molecule, which has at least two reactive endings, or by an electrostatic interaction, or by a complexing reaction or a combination thereof. Therefore, the substrate can be prepared so as it be able to anchor the thermal surface plasmon nanoparticle, and also the thermal surface plasmon nanoparticle can be prepared by the same way so as it be able to be anchored the substrate.

In an embodiment, the surface of the substrate is activated by cold plasma polymerization, e.g. activated by the deposition of molecules, like PFM (pentafluorophenyl methacrylate).

In an embodiment, the substrate or the thermal surface plasmon nanoparticle is functionalised with a functional molecule, the functional molecule preferable being a diamine derivative.

The medical device may be a surgical implant, a probe, a mesh, a suture, a straight forceps, medical needles, intravascular catheters, endotracheal tubes, and implants, prosthesis or any medical product useful in the medical field. In an embodiment, the medical device is a hemia mesh, prolapsed mesh, incontinence tape, wound dressings, vessel prostheses, stents, stent-grafts or the like. Beyond implants, surgical instruments are covered in the present invention by the term of medical devices. In an embodiment, the surface is of a medical device.

As described above, the thermal plasmonic nanoparticles to be bonded in the substrate may have a particle size ranging from 1 nm to 1 μm, more preferable from 1 nm to 100 nm. Therefore, according to the present invention a macro-surface of a substrate, for example a mesh, is decorated with thermal nanoparticles having a size of the order of nano or micro. Thus, the density of decorated thermal nanoparticles in the substrate may be modified up to a determinate value with the aim to control the rise of the temperature of the modified surface up to a predetermined value to kill or to avoid the attachment of a particular type of biofilm. The density of thermal nanoparticles decorated in the substrate may be from 10 to 1000 (thermal nanoparticles/ $\mu m^2$).

To understand the mechanism for reducing, killing or preventing the biofilm in the modified surface according the present invention, it should be understood that a biofilm which is attached to a substrate consists of many bacteria co-adhered by means of physical appendages and extracellular polymeric substances. Biofilm growth is governed by a number of physical, chemical and biological processes. The optimum temperature for a microorganism is associated with an increase in nutrient intake resulting in a rapid formation of biofilm. Nutrient metabolism is directly associated and dependent on the presence of enzymes. So it may be fair to say that the formation of a biofilm is dependent on the presence and reaction rates of enzymes. Temperature is correlated with the reaction rate of enzymes and so has a bearing on the development of the cells. Optimum temperatures result in the healthy growth of bacterial populations.

Conversely, temperatures away from the optimum reduce bacterial growth efficiency. This is due to a reduction in bacterial enzyme reaction rates. In addition to enzymes, environmental temperature affects the physical properties of the compounds within and surrounding the cells. Kisk o and O. Szab o-Szab o [*Biofilm removal of Pseudomonas strains using hot water sanitation*. Acta Univ. Sapientiae, Alimentaria, 4 (2011) 69-79] observed the cell number reduction of biofilms at high temperatures. In Planctonic cells of *P. aeruginosa* showed a 6-log reduction after hot water (85° C.) treatment. When *Pseudomonas aeruginosa* were adhered to stainless steel surface (cells attached to the surface reversible), the reduction was milder: 4.9. Biofilm cells showed the greatest resistance (3.2 log reduction) against 85° C. water treatment. Scher et al. [*Appl. Environ. Microbiol*. March 2005 vol. 71 no. 3, page 1163-1168] found similar results in *Salmonella* biofilms; heat treatments (at 70° C.) resulted in less than 5-log reduction after 40 min. Treatment at 80° C. killed all cells (8-log reduction) within 5 min or less. Also in Yeast-like cells (blastoconidia) of *C. albicans* growing exponentially on a glucose-containing medium underwent a dramatic loss of cellular viability when subjected to a severe heat stress (52.5° C. for 5 min) [Juan Carlos Argüelles Thermotolerance and trehalose accumulation induced by heat shock in yeast cells of *Candida albicans*. FEMS Microbiology Letters Volume 146, Issue 1, page 65-71, January 1997].

Therefore, it is of the general knowledge by a skilled person in this field determine the temperature which is required to reduce, to kill or to prevent the biofilm in each type of microorganism.

As described above, the thermal plasmonic nanoparticles to be bonded in the substrate may have a particle shape selected from a cylindrical, triangular, pyramidal, cubic, spherical, star shape, rod shape, or a combination thereof, or any other shape that may be able to be anchored in a substrate configured for this purpose.

As described above, the material of the thermal plasmonic nanoparticles may be of gold, silver, copper or any metal showing plasmon resonance effect on its surface; the material may be also a semiconductor, an oxide, a metal oxide or any other material showing plasmon resonance effect on its surface. Preferable, the thermal plasmonic nanoparticles are gold nanoparticle due to the fact that the gold nanoparticles are non toxic by themselves. The determination of which materials show plasmon resonance effect on its surface is of the general knowledge by a skilled person in this field.

Therefore, according to the present invention, the parameters of size, shape, or material of the thermal nanoparticles may be modified to modulate the rise temperature of the substrate up to a predetermined value. Furthermore, other parameters such as the source of light irradiated onto the modified surface may be also useful to further control the rise temperature of the substrate up to a predetermined value.

Hereinafter, the best mode for carrying out the present invention is described in detail.

In the best mode, the surface is the surface of a surgical implant. The surgical implant is a mesh having the modified surface, where the mesh being implanted into the body of a human. The mesh is made of polypropylene (PP).

In this embodiment, an activation of the polypropylene is carried out by cold plasma polymerization to get reactive chemical groups. On a second stage, the mesh is immersed in a diamino solution to get the presence of this reactive group on the surface. On a third stage, thermal gold nanoparticles are covalently attached to the mesh surface by anchorage to the reactive amino groups.

These thermal gold nanoparticles absorb light at 840 nm, which belongs to infrared spectrum. Under an irradiation at this wavelength, with laser or IPL (Intense Pulsed Light), the thermal gold nanoparticles become self-heating. A repetitive pulsed light turns the mesh into a bacteriostatic/bactericide surface. Gold nanoparticles are not toxic by themselves and the light irradiation in the infrared spectrum is no invasive, as a result it can be light irradiated repeatedly at any time after the implantation.

EXAMPLES

Nanoparticles are obtained by a well known 2-step seed mediated process. The nanorod dimensions and thus the absorption wavelength of the SPR can be taylored by varying the silver nitrate/ascorbic acid/seed ratios.

Preparation of the Seed:

Colloidal gold seeds were first prepared by mixing aqueous solutions of hexadecylcetyltrimethylammonium bromide (CTAB, 0.2 M, 5 mL) and hydrogen tetrachloroaurate (III) hydrate (0.5 mM, 5 mL) both kept at 27° C. A freshly prepared aqueous solution of sodium borohydride ($NaBH_4$, 0.01 M, 0.6 mL) was then added, previously cooled to 4° C., under vigorous stirring for 2 minutes. At this point the seed was allowed to settle for 2 hrs at 30° C. to allow remaining $NaBH_4$ to evolve. This yielded a gold nanoparticle suspension of sizes between 1-2 nm, which were used as seed for the preparation of nanoparticles. This solution will be further referred as Seed Suspension.

Thermal-Nanoparticle's Growth:

The "growth solution" was now prepared and consisted of CTAB (0.2 M, 20 mL), to which varying amounts of silver nitrate stock (4 mM) was added depending on desired nanoparticle aspect ratio and allowed to mix under mild stirring. Hydrogen tetrachloroaurate(III) hydrate (1 mM, 20 mL) was added and gave rise to a yellow/brown solution. Once ascorbic acid (79 mM, 0.29 mL) was added the yellow/brownish solution, the mixture should turn colorless. Next, 72 µL of aged Seed Suspension was added to the growth solution, mixed briefly and left undisturbed for 8 hrs at 30° C. to prevent CTAB crystallization. Initial color change of the mixture should be noted after ca. 10 min. This procedure yielded a nanoparticle suspension presenting an LSPR maximum at around 820 nm (±20 nm) and a maximum absorption of 1.6 AU.

Preparation of —COOH Mix Nanoparticles.

20 mL of the nanoparticles suspension obtained in Example 1 were centrifuged twice at 14000 rpm, 30 minutes. Each time the supernatant was removed and replaced by a 4 mM CTAB in water solution.

A solution mixture of the carboxylating reagents was prepared as follows: 97 mg of SH-PEG-COOH (Mw: 3000) and 3 mg of mercapto undecyl carboxylic acid (MUA) were dissolved in 10 mL of water and the pH was adjusted to 7.

The nanoparticles suspension (20 mL) was the added of 2 mL of the mixture of carboxylating reagents (10 mg/ml) and placed in an ultrasound bath at 45° C. The resulting mixture was sonicated during 30 minutes and then placed at 30° C. overnight.

The resulting carboxylated nanocomplex suspension was then centrifuged (14000 rpm, 30 minutes), the supernatant eliminated and finally redispersed with pure water to yield an absorption of around 3.5 AU at the SPR maximum.

Example 1

Mesh Modification by Thermal Gold Nanoparticles

Figure 2:
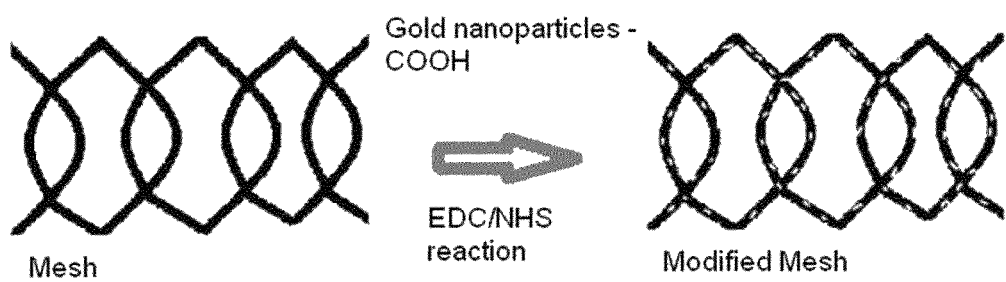
FIG. 2 is a schematic drawing of a mesh comprising a modified surface according to Example 1. In this figure, EDC/NHS reaction is the reaction of carboxyl-to-amine: Carbodiimides (EDC), and N-hydroxysuccinamide (NHS), a carboxyl-to-amine crosslinker group and an amine reactive crosslinker group, respectively.
Figure 3:
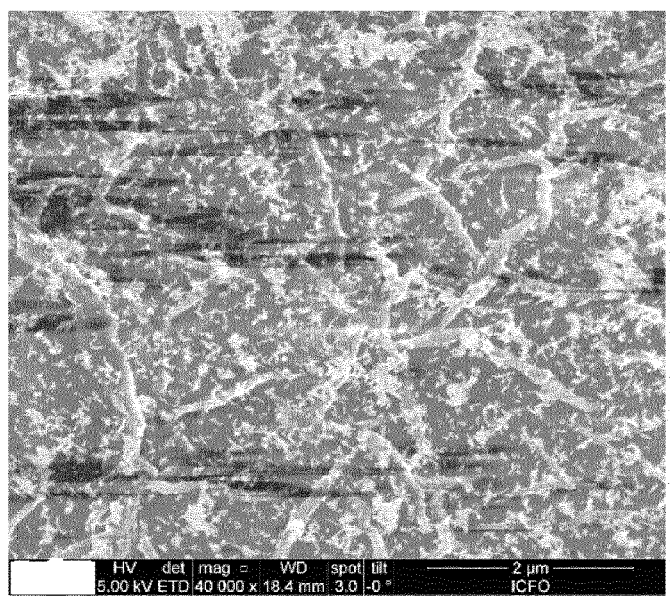
FIG. 3 shows the SEM (Scanning Electron Microscopy) of the modified mesh after modification with the EDC-NHS method (Example 1). The adhesion of nanorod aggregates is worth noticeable.

The above described thermal gold nanoparticles were anchored in a mesh for a surgical implant. The thermal gold nanoparticles were conjugated to the mesh by 1-ethyl-3-[3-dimethylaminopropyl] carbodiimide hydrochloride (EDC) and N-hydroxysulfosuccinimide reactions (NHS). Briefly, 5 mg de NHS y 10 mg of ECD were dissolved in 1 mL of buffer 50 mM phosphate pH 7. Short after 2 mL of the GNR's solution were added to the buffer solution. After this step, the meshes were plunged in that solution for 4 hours. Right after the mesh was wash with pure water to remove any unbounded thermal gold nanoparticle. FIGS. 2 and 3.

Example 2

Mesh Modification by Thermal Gold Nanoparticles

In this example, thermal gold nanoparticles obtained as described above and suspended in CTAB are linked to the amino modified mesh without further modification. The ability of metallic gold to complex with amino groups was exploited to form a great number of complex bonds leading to stable anchoring of gold nanoparticles to the mesh.

Figure 4:
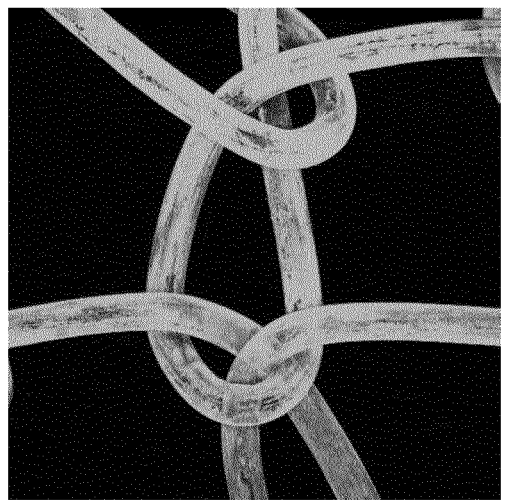
FIG. 4 shows the fluorescence microscopy of a mesh modified with thermal gold nanorods by complexation with amino groups according to Example 2. The anchoring of nanoparticles to the mesh was monitored by fluorescence microscopy. The intensity of the signal is proportional to the amount of thermal gold nanorods anchored on the surface.
Figure 5:
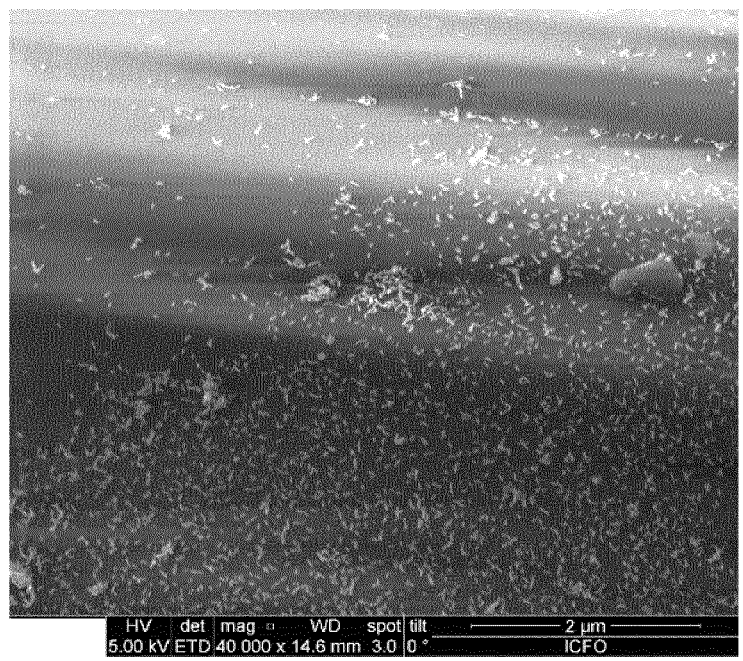
FIG. 5 shows the SEM (Scanning Electron Microscopy) microscopy of the mesh surface modified with thermal gold nanorods by the complexation method (Example 2), wherein a regular surface distribution is obtained compared to the EDC-NHS method (Example 1). More than 200 nanorods per µm² of mesh can be observed.
Figure 6:
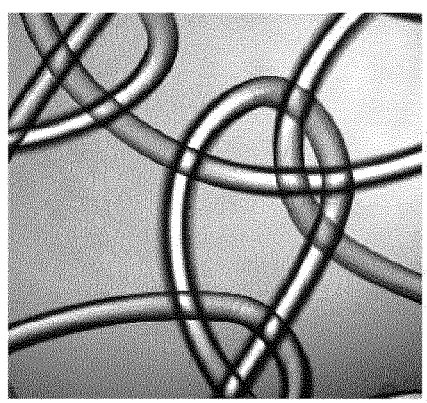
FIG. 6 shows nanorod amount anchored in a mesh by comparing two pictures a) with b), the right picture b) being through the fluorescence technique.
Figure 6:
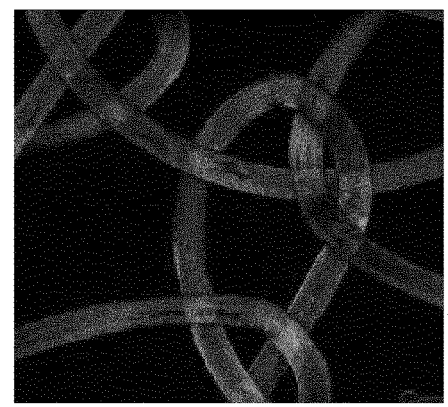
Figure 7:
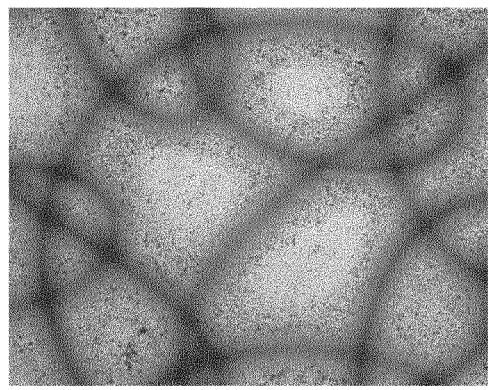
Figure 8:
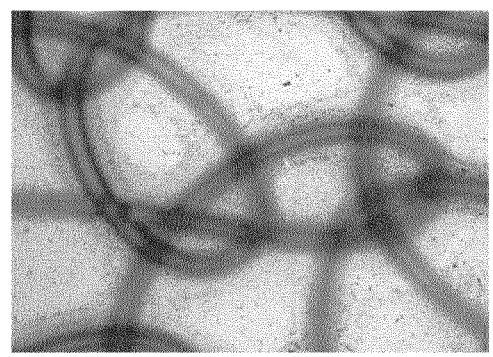

In practice, thermal gold nanoparticles suspended in CTAB after the growth step (100 mM CTAB) were centrifuged and the supernatant replaced by pure water to adjust the CTAB concentration to 3 mM and the nanoparticle concentration to an absorbance of 8 AU at 820 nm. The modified amino mesh was the added to this suspension and incubated overnight at 50° C. to perform the anchoring of thermal gold nanoparticles to the mesh. The mesh was then washed extensively with pure water. FIGS. 4 and 5.

Alternatively, the incubation time can be reduced by increasing the temperature or by addition of different quantities of ethanol to the incubation suspension up to 30%. In any case, the extent of the modification can be controlled by controlling the incubation time.

Bacteria's Growth and the Effect of the Irradiation of Light

Starting bacteria $S.$ $aureus$ $8.8 \times 10^8$ cfu/ml (conserved 4 days at 4° C. prior assay).

Culture liquid medium: Brain Heart Infusion Broth (BHI Broth).

Culture solid medium: Tryptic Soy Agar (TSA)

Petri dishes 6 cm and 10 cm.

All work is performed under sterile conditions, $S.$ $aureus$ is diluted with BHI Broth to $2.96 \times 10^6$ cfu/ml. Petri dishes of 6 cm (8) are prepared with around 3 mm thick TSA solid medium. In 2 dishes we placed untreated mesh (4 cm$^2$) and in other two dishes we placed the nanorods modified mesh (4 cm$^2$). All four assays were inoculated with 350 µl of $S.$ $aureus$ ($1.03 \times 10^6$ cfu) and then another slice of solid TSA is placed over the inoculated mesh to obtain an Agar sandwich. The 350 µl of inoculum seems to distribute correctly over all the Agar surface. The sandwiches are placed at 37° C. and incubated during 6 hours.

Two of the samples (mesh decorated or not with thermal nanoparticles) are treated with IPL (intense pulse light) at 1, 2, 3, 4, 5, 6 hours. Two IPL impacts on each side of the sandwich (11 joul/cm$^2$, 40 msec, light filtered at 755 nm). Those values are below the critical pain threshold when applied on the human skin.

The four samples of mesh are then recovered, washed slightly in 20 ml of sterile PBS and placed in 10 ml of PBS containing 2 mm sterile glass beads. To perform biofilm extraction samples are treated 2 minutes in an US bath 45 khertz and then 2 minutes at the vortex. The resulting suspension is then placed for culture in 10 cm agar Petri dishes (100 ul inoculum) at different dilutions in PBS 1:10, 1:100, all in duplicate.

Samples are stored at 37° C. and cfu counting is performed at 18 hours.

Results:

| Sample | 1:10 | cfu/plate | 1:100 | cfu/plate |
|---|---|---|---|---|
| No NC No IPL | TNTC | TNTC* | 195 | $11.88 \times 10^6$ |
| | TNTC | | 182 | |
| Nc + IPLSuppl | 10 | $9 \times 10^3$ | 1 | $5 \times 10^3$ |
| | 8 | | 0 | | cfu counting results for the second experiment
*TNTC: Too numerous to count

This experience shows an inhibition of $S.$ $aureus$ biofilm growth, (3-log of growth decrease) when the mesh is decorated with thermal gold nanorods and IPL by a thermal effect of the nanorods SPR resonance. FIGS. 7, 8, 9 and 10 demonstrate the effects when the modified surface according to the invention is light irradiated.

What is claimed is:

1. A modified surface capable of having bacteriostatic, bactericidal and antimicrobial activity upon light irradiation, wherein said modified surface comprises:
   a substrate's surface configured to anchor thermal nanoparticles supporting local surface plasmon resonance at its surface, wherein the material of the substrate possesses active groups on its surface to directly anchor the local surface plasmon nanoparticle, or the material of the substrate is previously prepared by a surface modification method to, then, anchor the local surface plasmon nanoparticle at its prepared surface; and, thermal nanoparticles supporting local surface plasmon resonance bonded to said substrate's surface forming a plasmonic meta-surface that supports surface plasmons to which light is coupled upon light irradiation, and that has a surface density of thermal nanoparticles per $\mu m^2$ ranging from 10 to 1000, thereby the modified surface being a meta-surface decorated with the thermal nanoparticles supporting local surface plasmon resonance, the thermal nanoparticles being able to increase their temperature by light irradiation in a wavelength range that matches with the wavelength of the local surface plasmon resonance of said nanoparticles, whereby said plasmonic meta-surface rises its temperature, allowing the temperature rise of said plasmonic meta-surface to avoid the attachment of a microorganism to this surface, to inhibit the formation of a biofilm on this surface and/or to destroy an already formed biofilm on this surface.

2. The modified surface according to claim 1, wherein said substrate is of fiber, woven, an alloy, a steel, a plastic, a polymer, a resin, a glass, a ceramic material or a combination thereof.

3. The modified surface according to claim 1, wherein said thermal nanoparticle has a particle size ranging from about 1 nm to about 1 µm.

4. The modified surface according to claim 1, wherein said thermal nanoparticle has a shape selected from the group consisting of a cylindrical, triangular, pyramidal, cubic, spherical, star shape, rod shape or a combination thereof.

5. The modified surface according to claim 1, wherein the material of said thermal nanoparticle is selected from the group consisting of gold, silver, copper, a semiconductor, an oxide, a metal oxide or a combination thereof.

6. The modified surface according to claim 1, wherein said thermal nanoparticles are bonded to said substrate by a covalent bond via a functional molecule, and wherein the functional molecule is selected from a bi-functional molecule or a functional molecule having at least two reactive endings.

7. The modified surface according to claim 1, wherein the light irradiation is from a source selected from a fluorescent or halogen lamp, a laser, an intense pulsed light, a light-emitting diode, an incandescent or chemiluminescence's light or a combination thereof.

8. A modified surface according to claim 1 being a non-medical device selected from a kitchen surface, piping, toys or any non-medical product.

9. The modified surface according to claim 1, wherein said thermal nanoparticles supporting surface plasmon resonance are bonded to said substrate's surface by an anchoring method not reversible.

10. The modified surface according to claim 1, wherein said thermal nanoparticles are bonded to said substrate's surface by a covalent bond via a functional molecule, or directly to the substrate's surface by an electrostatic interaction or a complexing reaction, or by a combination thereof.

11. A modified surface according to claim 1 being a medical device selected from a surgical implant, a prove, a mesh, a suture, medical needle, hernia mesh, prolapsed mesh, incontinence tape, wound dressing, stent, stent-graft, or a medical product.

12. A medical or non-medical device comprising a plasmonic meta-surface capable of having bacteriostatic, bactericidal and antimicrobial activity according to claim 1.

13. A method for modifying a surface capable of having bacteriostatic, bactericidal and antimicrobial activity according to claim 1, wherein the method comprises:
preparing a substrate's surface for anchoring thermal nanoparticles supporting local surface plasmon resonance;
selecting thermal nanoparticles supporting local surface plasmon resonance; and
bonding the selected thermal nanoparticles to said substrate's surface thereby forming a thermal coating, wherein the thermal coating has a density of thermal nanoparticles per $\mu m^2$ of the substrate's surface ranging from 10 to 1000,
the thermal nanoparticles being able to increase their temperature by light irradiation in a wavelength range that matches with the wavelength of the local surface plasmon resonance of said nanoparticles, whereby said thermal coating rises its temperature, allowing the temperature rise of said thermal coating to avoid the attachment of a microorganism to this surface, to inhibit the formation of a biofilm on this surface and/or to destroy an already formed biofilm on this surface.

14. The method according to claim 13, wherein the preparation of the substrate includes one or more of the following treatments:
activating the surface of the substrate by a surface modification method;
functionalising the surface of the substrate with a functional molecule, which has at least two reactive endings; or
functionalising the surface of thermal nanoparticles with a functional molecule, which has at least two reactive endings.

15. The method according to claim 14, wherein the surface modification method for activating the surface is selected from a treatment with active gases and vapours or irradiation; deposition of polymers from active gases and vapours; active gas or accelerated ion treatments; crosslinking of surface molecules; or mechanical methods; or chemical methods; or graft polymerization with radiation initiation or chemical initiation; or coating of the surface with an active component or coating matrix which contains active component.

16. The method according to claim 14, wherein the surface modification method is a cold plasma polymerization.

17. The method according to claim 14, wherein the functionalising the surface of the substrate or the functionalising the surface of the thermal nanoparticle is carried out with a functional molecule selected from a crosslinker, complex forming groups, groups able to form hydrogen bonds, or molecules containing ionic groups for ionic adsorption.

18. The method according to claim 14, wherein the functionalising the surface is carried out with a diamine derivative.

* * * * *